United States Patent
Canal et al.

(10) Patent No.: US 9,968,567 B2
(45) Date of Patent: May 15, 2018

(54) COMPOSITION BASED ON COQ10

(71) Applicant: ASOLTECH S.R.L., San Dorligo della Valle (IT)

(72) Inventors: Tiziana Canal, Trieste (IT); Fulvio Fortuna, Trieste (IT); Elena Mencini, Piacenza (IT)

(73) Assignee: ASOLTECH S.R.L., San Dorligo Della Valle (TS) (IT)

( * ) Notice: Subject to any disclaimer, the term of this patent is extended or adjusted under 35 U.S.C. 154(b) by 0 days. days.

(21) Appl. No.: 15/525,999

(22) PCT Filed: Nov. 13, 2015

(86) PCT No.: PCT/EP2015/025083
§ 371 (c)(1),
(2) Date: May 11, 2017

(87) PCT Pub. No.: WO2016/074800
PCT Pub. Date: May 19, 2016

(65) Prior Publication Data
US 2017/0319509 A1    Nov. 9, 2017

(30) Foreign Application Priority Data
Nov. 14, 2014   (IT) .............................. UD2014A0177

(51) Int. Cl.
| | | |
|---|---|---|
| A61K 31/122 | (2006.01) | |
| A61K 9/16 | (2006.01) | |
| A61K 9/14 | (2006.01) | |
| A61K 9/00 | (2006.01) | |

(52) U.S. Cl.
CPC .......... *A61K 31/122* (2013.01); *A61K 9/0053* (2013.01); *A61K 9/145* (2013.01); *A61K 9/146* (2013.01); *A61K 9/1623* (2013.01); *A61K 9/1652* (2013.01)

(58) Field of Classification Search
None
See application file for complete search history.

(56) References Cited

U.S. PATENT DOCUMENTS

| | | |
|---|---|---|
| 2007/0202166 A1 | 8/2007 | Heuer et al. |
| 2008/0248013 A1 | 10/2008 | Ikemoto et al. |
| 2009/0054530 A1 | 2/2009 | Parkhideh |
| 2009/0186009 A1 | 7/2009 | Sato et al. |

FOREIGN PATENT DOCUMENTS

| | | | |
|---|---|---|---|
| CN | 101172102 A | 5/2008 | |
| CN | 101940564 A | 1/2011 | |
| EP | 1364643 A1 | 11/2003 | |
| EP | 1782803 A1 | 5/2007 | |
| GB | 2402334 A | 12/2004 | |
| JP | 2005097121 A | 4/2005 | |
| JP | 2006232815 A | 9/2006 | |
| WO | 9803170 A1 | 1/1998 | |
| WO | 02067864 A2 | 9/2002 | |
| WO | 03097012 A1 | 11/2003 | |
| WO | 2007009997 A1 | 1/2007 | |
| WO | 2007086689 A1 | 8/2007 | |
| WO | 2013080028 A1 | 6/2013 | |
| WO | WO-2013080028 A1 * | 6/2013 | ............. A61K 8/732 |

OTHER PUBLICATIONS

S Onoue, A Uchida, K Kuriyama, T Nakamura, Y Seto, M Kato, J Hatanaka, T Tanaka, H Miyoshi, S Yamada. "Novel solid self-emulsifying drug delivery system of coenzyme Q10 with improved photochemical and pharmacokinetic behaviors." European Journal of Pharmaceutical Science, vol. 46, pp. 492-499. (Year: 2012).*
A Szuts, P Szabo-Revesz. Sucrose esters as natural surfactants in drug delivery systems—A mini-review. International Journal of Pharmaceutics, vol. 433, pp. 1-9. (Year: 2012).*
International Search Report and Written Opinion for International Application No. PCT/EP2015/025083 (13 Pages) (dated Feb. 9, 2016).

\* cited by examiner

*Primary Examiner* — Isaac Shomer
(74) *Attorney, Agent, or Firm* — Lucas & Mercanti, LLP (57) ABSTRACT

Ternary composition of CoQ10, one or more specific hydroxypropylcellulose (HPC) based amphiphilic carriers and one or more adjuvants selected from the group of sucrose esters.

23 Claims, 4 Drawing Sheets

COMPOSITION BASED ON COQ10

CROSS-REFERENCE TO RELATED APPLICATIONS

This application is a 371 of PCT/EP2015/025083, filed Nov. 13, 2015, which claims the benefit of Italian Patent Application No. UD2014A000177, filed Nov. 14, 2014.

FIELD OF THE INVENTION

Embodiments described herein relate to a composition based on Coenzyme Q10 (CoQ10 or simply Q10), also known as ubiquinone, ubidecarenone or, in its reduced form, ubiquinol, particularly, but not only, for use in nutritional, dietary, cosmetic, therapeutic, pharmaceutical and/or veterinary field.

BACKGROUND OF THE INVENTION

It is known that CoQ10—liposoluble substance—has been introduced into the clinical practice in Japan for patients having cardiac disorders and, in addition, it is presently used for a wide range of disorders and pathologies. For example, CoQ10 in combination with statins improves the haematochemical profile (cholesterol, HDL and nitric oxide levels), in the mitochondrial myopathies it improves the clinical picture, normalizing levels of lactate and creatine kinase, in the neurodegenerative diseases it showed encouraging results on key biochemical parameters of Parkinson's disease and, finally, in patients often suffering from migraine, it reduces the frequency of attacks and the days with headache and nausea. Moreover, CoQ10 may be useful in association with the conventional therapies, since, due its metabolic role, it may positively influence the progression of many diseases or it may prevent their onset. As an example, the antioxidant properties of CoQ10 in the cardiovascular disorders may end up being crucial in blocking the action of free radicals, which are responsible of dysfunctions in the endothelial tissue.

There are various techniques to provide formulations of CoQ10 as orally administrable forms. For example, the following scientific papers are available "Emulsification of coenzyme Q10 using gum arabic increases bioavailability in rats and human and improve food processing suitability" in J. Nutr. Sci. Vitaminol. 56, 41-47, 2010 and "Improvement of the oral bioavailability of coenzyme Q10 by emulsification with fats and emulsifiers used in the food industry" LWT-Food Science and Technology 42 (2009) 385-390.

In Onoue et al. ("Novel solid self-emulsifying drug delivery system of coenzyme Q10 with improved photochemical and pharmacokinetic behaviour", European Journal of Pharmaceutical Sciences 46 (2012) 492-499), a drug transport and delivery system of the solid auto emulsifying type (SEDDS) is described. In particular, a preformed emulsion containing CoQ10, as liposoluble active ingredient, MCT (Medium Chain Triglyceride), as oily phase, fatty acids sucrose ester as tensioactive agent, and hydroxypropylcellulose (HPC), as solid carrier, is spray-dried. In particular, the starting emulsion is prepared by pre-solubilizing CoQ10 (5 g), MCT (5 g) and sucrose ester (40 g) in ethanol (500 ml) and emulsifying this solution with HPC (50 g) dissolved in water (1,500 ml). Such liquid suspension is atomized in spray drops, thus obtaining a CoQ10/s-SEDDS system, wherein the macroscopic morphology is that of aggregated spherical particles, in which CoQ10 is present predominantly in form of dispersed particles and platelets, having a size from about 5 to 50 micrometers.

In this field the following patent applications are also available: EP-A-1782803, GB-A-2402334, US-A-2007/202166, US-A-2008/248013, US-A-2009/054530, US-A-2009/186009, WO-A-02/067864, WO-A-98/03170, WO-A-2007/086689 and CN-A-101940564 or CN-A-101172102.

However, for the above formulations the solution profiles have never been reported either due to their oily nature and poor hydrosolubility or due to the absence of a suitable dissolution medium. Moreover, such approaches result in long and expensive procedures, which often require the use of solvents or solvent mixtures, which have to be removed to obtain a solid system and traces of which may remain in the final product. In alternative, such procedures may require the use of high temperatures, which may risk degrading the final product.

Finally, in many such procedures it is necessary to use more than three components to obtain the desired result or high concentrations of surfactants or carriers, which limit the content of CoQ10 to very low levels.

In the attempt to solve the technical problems relating to the preparation of compositions in the form of fine powders comprising active ingredients substantially poorly soluble in water and organic solvents, a process of dry co-grinding has been described in the International patent application WO-A-03/097012 (WO'012), wherein an active ingredient is included in a hydrophilic or hydrophobic carrier, depending on the chemical-physical characteristics of the active ingredient, in the presence of a co-grinding auxiliary substance, which allows a drastic reduction of the co-grinding time with indisputable advantages for the stability of the active ingredient.

The international patent application WO-A-07/009997 (WO'997) describes the application of such technique to antioxidant agents, including CoQ10 to obtain compositions in form of fine powder easily dispersible and possibly soluble in water, which have shown significant increase in antioxidant power for the same concentration of active ingredient in solution.

The international patent application WO-A-2013/080028 (WO'028) describes a composition based on ubidecarenone, consisting of CoQ10, one or more specific carriers selected from the group of maltodextrins and one or more adjuvant agents selected from the group of sucrose esters. In WO'028 examples of compositions based on ubidecarenone are also reported, which consist of CoQ10, hydroxypropylmethyl cellulose (HPMC) and one or more adjuvant agents selected from the group of sucrose esters. However, such compositions are described in WO'028 as less performing than those containing maltodextrins due to their lower solubility and the jellifying capability of the carrier hydroxypropylmethyl cellulose.

Therefore, there is in the field the consistent need to provide a composition based on CoQ10 together with its preparation method, which, on one hand, could improve the solubility and dissolution of CoQ10, and on the other hand could be prepared in an efficient, rapid and economical way.

There is, therefore, a need to improve a composition based on CoQ10, which could overcome at least one of the disadvantages of the state of the art.

In particular, a purpose of the present invention is to provide a new composition based on CoQ10 and to develop a method for its preparation, which allows obtaining a high solubility and dissolution of CoQ10.

To obviate the drawbacks of the state of the art and to obtain these and further advantages, the Applicant has now considered, implemented and tested the present invention.

Unless otherwise indicated, all the technical and scientific terms used here and hereafter have the same meaning commonly understood by a person having ordinary skill in the art, to which the present invention belongs. Even if methods and materials similar or equivalent to those herein described maybe used in the practice or in the tests of the present invention, hereinafter materials and methods are described as examples. The materials, methods and examples have purely illustrative purposes and must not be construed in a limitative way.

The word "to comprise" and variants of the word, such as "comprises" and "comprising" are used here to indicate the inclusion of a clearly expressed whole or clearly expressed wholes, but not the exclusion of any other whole or any other wholes, unless in the context or in use an exclusive interpretation of the word is required.

The word "to consist" and variants of the word, such as "consists" and "consisting" are used here to indicate the inclusion of a clearly expressed whole or clearly expressed wholes and the exclusion of any other whole or any other wholes.

SUMMARY OF THE INVENTION

The present invention is set forth and characterized in the independent claims, while the dependent claims describe other characteristics of the present invention or variants of the main embodiment.

In accordance with some embodiments, a ternary composition is provided. According to a form of embodiment, the aforementioned ternary composition consists of CoQ10, one or more specific hydroxypropylcellulose (HPC) based amphiphilic carriers and one or more adjuvants selected from the group of sucrose esters.

According to a form of embodiment, the aforementioned ternary composition is for the use in one or more of the following fields: nutritional, dietetic, cosmetic, therapeutic, pharmaceutical and/or veterinary.

According to forms of embodiments, a method for the preparation of a ternary composition is described. According to a form of embodiment, the method provides exclusively the use of CoQ10, one or more specific hydroxypropylcellulose based amphiphilic carriers and one or more adjuvants selected from the group of sucrose esters.

According to a form of embodiment, the method provides the co-grinding of said CoQ10, one or more specific hydroxypropylcellulose based amphiphilic carriers and one or more adjuvants selected from the group of sucrose esters.

According to a form of embodiment, the method provides subjecting to dry co-grinding, preferably co-grinding together at the same time, CoQ10, one or more specific hydroxypropylcellulose based amphiphilic carriers and one or more adjuvants selected from the group of sucrose esters.

According to another form of embodiment, the method provides a technique selected from extrusion, granulation, kneading, spray-drying for the processing of said CoQ10, one or more specific hydroxypropylcellulose based amphiphilic carriers and one or more adjuvants selected from the group of sucrose esters.

These and other aspects, features and advantages of the present disclosure will be better understood with reference to the following description, drawings and attached claims. The drawings, which are incorporated and form part of the present invention, illustrate some embodiments of the present subject matter and, together with the description, are intended to show the principles of the disclosure.

The various aspects and features described in this disclosure may be applied individually, where possible. These individual aspects, such as aspects and features present in the description or in the attached dependent claims, may be the subject of divisional applications.

It is noted that any aspect or feature already known during the patenting procedure is meant not to be claimed and to be the subject of a disclaimer.

DETAILED DESCRIPTION OF THE INVENTION

Reference is now made in detail to the various embodiments of the invention, one or more examples of which are described hereinafter. Each example is provided by way of illustration of the invention and is not intended as a limitation of the same. For example, the features illustrated and described as part of one embodiment may be adopted on, or in association with, other embodiments to produce a further embodiment. It is understood that the present invention will be inclusive of such modifications and variations All measurements are made, unless otherwise indicated, at 25° C. and atmospheric pressure. All the temperatures, unless otherwise stated, are expressed in degrees Celsius.

All the percentages and the ratios quoted are referred to the weight of the total composition (w/w), unless otherwise indicated.

All the percent ranges listed herein are provided with the proviso that the sum with respect to the total is 100%, unless otherwise indicated.

All ranges reported here are inclusive of extremes, including those that show a range "between" two values, unless otherwise indicated.

Also included in the present description are the intervals that result from the overlapping or union of two or more intervals described, unless otherwise indicated.

Also included in the present description are the intervals that may result from the combination of two or more point values described, unless otherwise indicated.

Terms such as "approximately", "generally", "substantially" and the like are to be understood in their capacity to change a word or value that is not absolute, but is not reported in the prior art. Such terms will be defined by the specific circumstances and the terms that they intend to change according to the common meaning of those terms in the field. They will cover at least the degree of expected experimental error, the technical error and instrument error for a given technique used to measure a value. Unless otherwise stated, in this description, the terms "a", "an", "one" shall be deemed inclusive of the plural forms, unless the context suggests otherwise.

In accordance with the present description, embodiments are related to a ternary composition consisting of CoQ10, one or more specific hydroxypropylcellulose based amphiphilic carriers and one or more adjuvants selected from the group of sucrose esters.

It is noted that, hereafter, reference will be made to coenzyme Q10, or CoQ10, or even more briefly Q10, also known as ubiquinone, ubidecarenone or as its reduced form, that is ubiquinol.

Therefore in possible embodiments, combined with all the embodiments here described, it may be provided that, in place of the ubidecarenone or ubiquinone, the reduced form, called ubiquinol can be used.

Hereinafter, for the sake of brevity, reference may be made to the term "HPC" indicating in general a hydroxypropylcellulose based amphiphilic carrier.

Furthermore, in accordance to the present description, this definition being true for all the embodiments described here, with the term sucrose ester it is meant an ester of sucrose and a advanced organic acid, normally in form of odourless and tasteless white powders. Usually, the sucrose ester can have emulsifying properties.

Possible forms of embodiment, that can be combined with all embodiments described herein, can refer to a ternary composition consisting of CoQ10 in reduced form, i.e. ubiquinol, one or more specific hydroxypropylcellulose based amphiphilic carriers and one or more adjuvants selected from the group of sucrose esters.

The Applicant has found that the ternary composition of the present invention, and in particular the CoQ10 contained in it, exhibits a remarkable increase of solubility with respect to the composition obtained according to the known technique. In other words, it was found that in the ternary composition of the present invention, CoQ10 is rendered more soluble in water; therefore, CoQ10 is more absorbable, thus improving, consequently, at the same dosage, its availability in the organism.

In possible embodiments, combinable with all the embodiments described herein, the ternary composition may provide a weight percentage of CoQ10 between 10% and 60%, in particular between 10% and 55%, more in particular between 25% and 50%, even more in particular between 30% and 40%.

In possible embodiments, combinable with all the embodiments described herein, the ternary composition may provide a weight percentage of one or more specific HPC based amphiphilic carriers between 10% and 80%, in particular between 20% and 70%, more in particular between 30% and 60%, likewise more particularly between 40% and 50%.

In possible embodiments, combinable with all the embodiments described herein, the ternary composition may provide a weight percentage of one or more adjuvants selected from the group of sucrose esters of between 10% and 40%, in particular between 20% and 30%.

In some embodiments, combinable with all the embodiments described herein, the weight ratio between CoQ10 and sucrose esters in the ternary composition in accordance with the present description may be less or equal to 1, for example between 0.5 and 1.

In further embodiments, combinable with all the embodiments described herein, the weight ratio between CoQ10 and sucrose esters in the ternary composition in accordance with the present description may be higher or equal to 1, for example between 1 and 6.

In possible embodiments, combinable with all the embodiments here described, the ternary composition may provide a weight ratio between CoQ10 and sucrose ester from 0.5:1 to 6:1, in particular from 0.5:1 to 5:1, more in particular from 0.5:1 to 4:1, even more particularly from 0.5:1 to 3:1.

In possible embodiments, combinable with all the embodiments here described, the ternary composition may provide a weight ratio between CoQ10 and sucrose ester from 0.75:1 to 6:1, in particular from 0.75:1 to 5:1, more in particular from 0.75:1 to 4:1, even more particularly from 0.75:1 to 3:1.

In possible embodiments, combinable with all the embodiments here described, the ternary composition may provide a weight ratio between CoQ10 and sucrose ester from 1:1 to 6:1, in particular from 1:1 to 5:1, more in particular from 1:1 to 4:1, even more particularly from 1:1 to 3:1.

Embodiments in accordance with the present description may provide CoQ10 at 10%, HPC at 80% and sucrose ester at 10% by weight. This specific embodiment is here also reported as a ternary composition of CoQ10/HPC/sucrose ester 1/8/1, or simply 1/8/1, referring to the weight/weight ratio (w/w).

Embodiments in accordance with the present description may provide CoQ10 at 15%, HPC at 70% and sucrose ester at 15% by weight. This specific embodiment is here also reported as a ternary composition of CoQ10/HPC/sucrose ester 1.5/7/1.5, or simply 1.5/7/1.5, making referring to the weight/weight ratio (w/w).

Embodiments in accordance with the present description may provide CoQ10 at 20%, HPC at 60% and sucrose ester at 20% by weight. This specific embodiment is here also reported as a ternary composition of CoQ10/HPC/sucrose ester 2/6/2, or simply 2/6/2, referring to the weight/weight ratio (w/w).

Embodiments in accordance with the present description may provide CoQ10 at 25%, HPC at 50% and sucrose ester at 25% by weight. This specific embodiment is here also reported as a ternary composition of CoQ10/HPC/sucrose ester 2.5/5/2.5, or simply 2.5/5/2.5, referring to the weight/weight ratio (w/w).

Embodiments in accordance with the present description may provide CoQ10 at 30%, HPC at 40% and sucrose ester at 30% by weight. This specific embodiment is here also reported as a ternary composition of CoQ10/HPC/sucrose ester 3/4/3, or simply 3/4/3, referring to the weight/weight ratio (w/w).

Embodiments in accordance with the present description may provide CoQ10 at 33%, HPC at 33% and sucrose ester at 33% by weight. This specific embodiment is here also reported as a ternary composition of CoQ10/HPC/sucrose ester 3.3/3.3/3.3, or simply 3.3/3.3/3.3, referring to the weight/weight ratio (w/w). Here and hereafter value 33% can approximately be used to indicate the value 33.3%.

Embodiments in accordance with the present description may provide CoQ10 at 40%, HPC at 20% and sucrose ester at 40% by weight. This specific embodiment is here also reported as a ternary composition of CoQ10/HPC/sucrose ester 4/2/4, or simply 4/2/4, referring to the weight/weight ratio (w/w).

Embodiments in accordance with the present description may provide CoQ10 at 50%, HPC at 10% and sucrose ester at 40% by weight. This specific embodiment is here also reported as a ternary composition of CoQ10/HPC/sucrose ester 5/1/4, or simply 5/1/4, referring to the weight/weight ratio (w/w).

Embodiments in accordance with the present description may provide CoQ10 at 50%, HPC 20% and sucrose ester at 30% by weight. This specific embodiment is here also reported as a ternary composition of CoQ10/HPC/sucrose ester 5/2/3, or simply 5/2/3, referring to the weight/weight ratio (w/w).

Embodiments in accordance with the present description may provide CoQ10 at 50%, HPC at 30% and sucrose ester at 20% by weight. This specific embodiment is here also reported as a ternary composition of CoQ10/HPC/sucrose ester 5/3/2, or simply 5/3/2, referring to the weight/weight ratio (w/w).

Embodiments in accordance with the present description may provide CoQ10 at 50%, HPC at 40% and sucrose ester at 10% by weight. This specific embodiment is here also reported as a ternary composition of CoQ10/HPC/sucrose ester 5/4/1, or simply 5/4/1, referring to the weight/weight ratio (w/w).

Embodiments in accordance with the present description may provide CoQ10 at 60%, HPC at 10% and sucrose ester at 30% by weight. This specific embodiment is here also reported as a ternary composition of CoQ10/HPC/sucrose ester 6/1/3, or simply 6/1/3, referring to the weight/weight ratio (w/w).

Embodiments in accordance with the present description may provide CoQ10 at 60%, HPC at 20% and sucrose ester at 20% by weight. This specific embodiment is here also reported as a ternary composition of CoQ10/HPC/sucrose ester 6/2/2, or simply 6/2/2, referring to the weight/weight ratio (w/w).

Embodiments in accordance with the present description may provide CoQ10 at 60%, HPC at 30% and sucrose ester at 10% by weight. This specific embodiment is here also reported as a ternary composition of CoQ10/HPC/sucrose ester 6/3/1, or simply 6/3/1, referring to the weight/weight ratio (w/w).

Embodiments described herein may provide further possible percentage ranges by weight of CoQ10, HPC and sucrose ester included or that overlap within the ranges mentioned above.

In some embodiments, the weight percentages of one or more specific hydroxypropylcellulose based amphiphilic carriers and sucrose esters in the composition of the present invention can be selected so that at the increase of the first, the second might decrease.

In some embodiments, one or more adjuvants selected from the class of sucrose esters can be one or more among sucrose monopalmitate, sucrose monostearate, sucrose dipalmitate, sucrose distearate, alkylated sucrose, or mixtures of two or more of them.

Exemplary embodiments, which may be combined with other embodiments described herein, may provide that one or more adjuvants selected from the class of sucrose esters are a sucrose ester or mixture of sucrose esters having a HLB (Hydrophilic-Lipophilic Balance) value between 14 and 16.

Embodiments of the ternary composition in accordance with the present description, which consist of the aforementioned three components, or classes of compounds, provide exclusively for the above components CoQ10, hydroxypropylcellulose, and sucrose ester(s) as main components, without excluding, however, in some variant embodiments, that the composition of the present invention may be associated with, assembled or mixed with, additional auxiliary components, for example to develop the desired product, for example as a nutritional supplement, for pharmaceutical, therapeutic or veterinary use.

In forms of embodiments, which may be combined with other embodiments described herein, the composition of the present invention is a unique ternary composition and consists of three components or classes of components, namely CoQ10, one or more specific hydroxypropylcellulose based amphiphilic carriers, and one or more adjuvants selected from the group of sucrose esters. Here and hereinafter, the expression ternary composition shall mean a composition according to the present invention, which consists of CoQ10, one or more specific hydroxypropylcellulose based amphiphilic carriers, and one or more adjuvants selected from the class of sucrose esters.

In yet further embodiments, a ternary composition, which includes CoQ10, one or more specific hydroxypropylcellulose based amphiphilic carriers and one or more adjuvants selected from the class of sucrose esters may be provided.

In embodiments, which may be combined with other embodiments described herein, the composition of the present invention consists of CoQ10, one or more specific hydroxypropylcellulose based amphiphilic carriers and one or more adjuvants selected from the class of sucrose ester and can be used for the development of a formulation or product, being associated with, assembled or mixed with, one or more substances, such as active or auxiliary, further selected from a group comprising:

Vitamins, such as one or more of: vitamin A, vitamin B1, vitamin B2, vitamin B3 (PP, nyacin), vitamin B5 (pantothenic acid), vitamin B6, vitamin B12, vitamin C, vitamin D, vitamin E and vitamin H, and/or Mineral or metals, such as one or more of: magnesium, potassium, zinc, selenium, calcium, fluorine, phosphor, iron and iodine, and/or Nutritional supplements, additional antioxidants plant extracts and/or preparations and/or herbal preparations, such as one or more among: lactoferrin, berberine, berberine hydrochloride, silymarin, monacolin, folic acid, astaxanthin, policosanol(s), sinensetin, essential omega-3 fatty acid, for example EPA e DHA, and/or omega-6, resveratrol, L-carnitine, acetyl L-carnitine, propionyl L-carnitine, acetyl L-carnitine taurinate, L-carnitine tartrate, creatine, carnosine, L-aspartic acid, L-asparagine, *Monascus purpureus*, diosmin, hesperidin, troxerutin, glutamine, phosphoserine, *Gingko biloba* (dry extract) and caffeine.

With the expression "to associate" or "to put together" it is meant that the ternary composition according to the present description is used by adding to it one or more of the substances listed above, without nevertheless impairing the ternary composition, in other words the one or more added substances do not interfere with the ternary equilibrium and do not modify the synergy among the components of the ternary composition, so that the final formulation comprises in all respects the ternary composition in itself and the one or more above indicated substances.

In the case of active ingredient it is intended that the composition of the present invention is in association, mixed or put together with said additional substances in one formulation, whereas in the case of auxiliary substance it is intended that the ternary composition of the present invention may further comprise such additional substances.

Specific examples of components or substances, active or auxiliary, associable, mixed or put together with the composition of the present invention in the case of use in the alimentary or dietary supplementation, are comprised in or may be selected among the group comprising: lactoferrin, berberine, berberine hydrochloride, silymarin, monacolin, folic acid, astaxanthin, policosanol(s) sinensetin, omega-3, resveratrol, L-carnitine, acetyl L-carnitine, propionyl L-carnitine, acetyl L-carnitine taurinate, L-carnitine tartrate, creatine, carnosine, L-aspartic acid, L-asparagine, *Monascus purpureus*, diosmin, hesperidin, troxerutin, glutamine, phosphoserine, *Gingko biloba* (dry extract), caffeine, vitamin A, vitamin B5 (panthotenic acid), vitamin B12, vitamin C, vitamin E, vitamin B6, magnesium, potassium, zinc, selenium, iron and iodine.

Forms of embodiments described herein are relative to a formulation, which comprises the ternary composition according to the present description and one or more of the cited components, active ingredients or auxiliary substances here described.

An embodiment may provide a formulation, which comprises the ternary composition of the present invention and berberine hydrochloride, astaxanthin, monacoline, policosanol and folic acid.

A form of embodiment may provide a formulation, which comprises the ternary composition according to the present invention and astaxanthin, monacolin, policosanol and folic acid.

A form of embodiment may provide a formulation, which comprises the ternary composition according to the present description and berberine hydrochloride, sinensetin, monacolin, policosanol and folic acid.

A form embodiment may provide a formulation, which comprises the ternary composition described in the present invention and omega-3, resveratrol, policosanols, L-carnitine, *Monascus purpureus*, folic acid, vitamin B6 and vitamin B12. This form of embodiment can be useful for maintaining the physiological balance of cholesterol and homocysteine levels, contributing to the normal cardiac function. Moreover, such embodiment may counteract the oxidative processes and promote the control of the lipidic profile.

A form of embodiment may provide a formulation, which comprises the ternary composition of the present description and resveratrol, lactoferrin, zinc, vitamin E vitamin C and vitamin E. Such form of embodiment may promote the ability of the organism to counteract aggressive factors and the attack of infective agents, when such ability is reduced due to stress, age, diseases, inflammation, smoke and other factors linked to life style, conditions that increase the production free radicals.

A form of embodiment may provide a formulation, which comprises the ternary composition of the present description and acetyl L-carnitine taurinate, creatine, carnosine, L-aspartic acid, L-asparagine, vitamin B5, vitamin E, selenium, zinc, magnesium and potassium. Such form of embodiment may be useful for restoring in the body the appropriate amount of supports for the production of energy. Moreover, such form of embodiment may provide a metabolic support promoting the recovery of the cells energetic power, allowing the elimination and counteracting the formation of free radicals and restoring in the body the metabolic factors essential for the proper functioning of the energy producing processes.

A form of embodiment may provide a formulation, which comprises the ternary composition of the present invention and diosmin, hesperidin, troxerutin and L-carnitine tartrate. Such form of embodiment may be useful for the maintenance of the physiological venous circulation promoting processes of small venous vessels protection. Moreover, such form of embodiment may provide useful elements for increasing the venous tone, the lymphatic drainage and the microcirculatory flow.

A form of embodiment may provide a formulation, which comprises the ternary composition of the present description and magnesium, glutamine, phosphoserine, *Gingko biloba* (dry extract) and vitamin B6. Such form of embodiment may contribute the psychological and mental functions, concentration, memory and learning.

A form of embodiment may provide a formulation, which comprises the ternary composition according to the present description and acetyl L-carnitine and propionyl L-carnitine.

A form of embodiment may provide a formulation, which comprises the ternary composition according to the present description and vitamin B5 (pantothenic acid), iron, zinc, iodine, caffeine and phosphoserine. Such form of embodiment may be indicated in particular to promote the normal cognitive function and to reduce tiredness and fatigue.

A method for preparing a ternary composition, which foresees the use of CoQ10, one or more specific hydroxypropylcellulose based amiphiphilic carriers and one or more adjuvant agents selected from the group of sucrose esters is also in the spirit of the present invention.

The composition of the present invention may be obtained by techniques such as dry co-grinding, as described in the applications WO'012 and WO'997, here entirely incorporated as reference, or by extrusion, granulation and kneading, spray drying or others.

In forms of embodiment, dry co-grinding may foresee that an active ingredient, such as CoQ10, is included in a carrier, such as hydroxypropylcellulose based amiphiphilic carrier, in the presence of a co-grinding auxiliary substance, such as sucrose ester, which allows a drastic reduction of the co-grinding time with undisputable advantages for the stability of the active ingredient.

In exemplary and non-limitative forms of the present invention, the dry co-grinding is a technique particularly suitable for obtaining the form of embodiments described herein, mainly because it does not make use of solvents nor does it imply any heating of the components. In such a case, it is preferable to co-grind together at the same time the three components or classes of components of the composition, CoQ10, hydroxypropylcellulose based amphiphilic carrier and sucrose ester, rather than co-grind separately sucrose esters and the co-ground binary system CoQ10 and hydroxypropylcellulose based amphiphilic carrier. In such a way, in fact, the sucrose ester has a more predominant role as a co-grinding adjuvant agent. The co-grinding technique may also provide advantages in terms of solubility and release of the active ingredient.

Therefore, a preferred embodiment of the present invention is a ternary composition consisting of CoQ10, one or more hydroxypropylcellulose (HPC) based amphiphilic carriers and one or more adjuvants selected from the group of sucrose esters, wherein said ternary composition is obtained by co-grinding CoQ10, hydroxypropylcellulose based amphiphilic carrier and sucrose ester.

The powder composition of the present invention may be packaged as such or mixed to acceptable excipients and conveniently formulated in any form suitable for oral administration, including solid forms, such as powders, granulates, sachets, stick-pack, flow-pack, capsules, tablets and, optionally, normal or controlled release, for example time-, pH-dependent, or filmed or gastro-protective, colon-specific release or multilayer, chewing gum or candies, or liquid forms, such as syrups, drops, elixirs, solutions and suspensions in general.

Moreover, the composition of the present invention may be incorporated in other formulations such as creams, ointments, gels, pastes, water based creams, emulsions, serums, face powders, spray and the like, suppositories, ovules, transdermal patches and the like, toothpastes, periodontal gels and mouth washes.

The composition of the present invention, as such or mixed with acceptable excipients and appropriately formulated, may be used in any form suitable to alimentary and dietary supplementation.

In forms of embodiments, the powder composition of the present invention, as such or mixed with acceptable excipients and appropriately formulated, may be used in any form suitable for cosmetic use.

Finally, the powder composition of the present invention packaged as such, or produced in its ternary form, mixed to excipients and appropriately formulated, may be used in any form suitable for pharmaceutical use, optionally also for veterinary use.

Forms of embodiments combinable with all the forms of embodiments here described, relate to the ternary composition according to the present description or to the formulation comprising such ternary composition, for use in the cardiovascular treatment. In particular, forms of embodiments here described are advantageous in cardiovascular situations, which lead to the reduction or the blockade of the metabolic synthetic pathways or use of CoQ10. Therefore, forms of embodiments here described by making CoQ10 more available, may be efficacious for:

Cardiovascular treatment of post-AMI (acute myocardial infarction) and post-PTCA (percutaneous transluminal coronary angioplasty) or coronary post-surgery in the prevention of reperfusion damages and in the myocardial oxygenation;

Cardiovascular treatment in case of congestive heart failure (CHF) for the improvement of inotropism and the ventricular ejection fraction (VEF);

Cardiovascular treatment in cardiac patients undergoing chronic dyslipidaemia treatment with statins.

Forms of embodiments, combinable with all the forms of embodiments here described, relate to the ternary composition according to the present description or to the formulations comprising such ternary composition for the use as adjuvant in the cardiovascular field for the treatment of:

Cardiotoxicity from chemotherapeutical and/or radio therapeutical agent;

Post-surgery asthenia in cardiac patients or patients at high risk to develop cardiac diseases or in elderly patients or oncological patients;

Asthenia in cardiac, neurologic and/or orthopaedic patients in functional re-educational phase;

Chronic asthenia from cardio circulatory and muscular deficit in elderly subjects.

Forms of embodiment, combinable with all the forms of embodiments here described, relate to the ternary composition according to the present description or to the formulations comprising such ternary compositions, for the use as adjuvant agents for:

Improving cellular respiration,

Producing cell energy,

Antioxidant action (ROS),

Epithelium protective and/or anti-inflammatory recovering action,

Treatment of the mucous membranes and/or skin, in particular, but not only, pathologies of the oral mucous membrane, for example aphthosis of the oral cavity, more in particular for stomatitis, gingivitis and periodontitis.

The following non-limitative Examples will refer to some Figures/Drawings, whose description is reported here below.

DESCRIPTION OF THE FIGURES

FIG. 2: it shows the comparison graphs of DRT for compositions obtained by co-grinding, in particular, Examples 1-4 with HPC (dashed lines), Examples A1-A3, Examples B2-B3. In the legend in FIG. 2 the number after the acronym/name of the carrier indicates the % w/w CoQ10 and in brackets the example, to which the graph refers to.

FIG. 3: it shows the comparison graphs of DRT between the compositions obtained by co-grinding and those obtained by spray-drying (HPC-MDX), in particular, Examples 2, 3, 6, 7 with HPC, Examples A2-A3 and Examples C1-C2 with MDX. In FIG. 3, the solid lines identify the graphs of the co-ground compositions, while the dotted lines identify the graphs of the spray-dried compositions. Also in the legend in FIG. 3 the number after the acronym/name of the carrier indicates the w/w % CoQ10 and the one between brackets the example to which the graph refers to.

FIG. 4: it shows the comparison graphs of DRT between the compositions obtained by co-grinding and those obtained by spray-drying (HPC-HPMC), in particular, Examples 2, 3, 6, 7 with HPC, Examples B2-B3 and Examples D1-D2 with HPMC. In FIG. 4, the solid lines identify the graphs of the co-ground compositions, while the dotted lines identify the graphs of the spray-dried compositions. Also in the legend in FIG. 4 the number after the acronym/name of the carrier indicates the w/w % CoQ10 and the one between brackets the example to which the graph refers to.

EXAMPLES

Example 1: Composition of the Present Invention Obtained by Co-Grinding

Ternary Composition of CoQ10/HPC/Sucrose Ester 1/8/1.

For the preparation of the ternary composition of said example, 15 g of a mixture in w/w ratio 1/8/1 of CoQ10 (1.5 g, 10%), HPC (12 g, 80%) and sucrose ester (1.5 g, 10%) obtained for example using a rotating body mixer, were loaded into a jar of a planetary mill and subjected to mechano-chemical activation for 30 minutes at a speed of 200 rpm. At the end of the process, the product in the form of fine powder was unloaded and sieved. A ternary compound material CoQ10/HPC/sucrose ester was obtained in a w/w ratio 1/8/1 with a 10% by weight CoQ10 titre.

Example 2: Composition of the Present Invention Obtained by Co-Grinding

Ternary Composition of CoQ10/HPC/Sucrose Ester 1/2/1.

For the preparation of the ternary composition of said example, 15 g of a mixture in w/w ratio 1/2/1 of CoQ10 (3.75 g, 25%) HPC (7.5 g, 50%) and sucrose ester (3.75 g 25%), obtained for example using a rotating body mixer, were loaded into a jar of a planetary mill and subjected to mechano-chemical activation for 30 minutes at a speed of 200 rpm. At the end of the process, the product in the form of fine powder was unloaded and sieved. A ternary compound material CoQ10/HPC/sucrose ester was obtained in a w/w ratio 2.5/5.0/2.5 with a 25% by weight CoQ10 titre.

Example 3: Composition of the Present Invention Obtained by Co-Grinding

Ternary Composition of CoQ10/HPC/Sucrose Ester 1/1/1.

For the preparation of the ternary composition of said example, 15 g of a mixture in w/w ratio 1/1/1 of CoQ10 (5 g, 33.3%) HPC (5 g, 33.3%) and sucrose ester (5 g, 33.3%), obtained for example using a rotating body mixer, were loaded into a jar of a planetary mill and subjected to mechano-chemical activation for 30 minutes at a speed of 200 rpm. At the end of the process, the product in the form of fine powder was unloaded and sieved. A ternary compound material CoQ10/HPC/sucrose ester was obtained in a w/w ratio 1/1/1 with a 33.3% by weight CoQ10 titre.

Example 4: Composition of the Present Invention Obtained by Co-Grinding

Ternary Composition of CoQ10/HPC/Sucrose Ester 1/0.5/1.

For the preparation of the ternary composition of said example, 15 g of a mixture in w/w ratio 1/0.5/1 of CoQ10 (6 g, 40%) HPC (3 g, 20%) and sucrose ester (6 g, 40%), obtained for example using a rotating body mixer, were loaded into a jar of a planetary mill and subjected to mechano-chemical activation for 30 minutes at a speed of 200 rpm. At the end of the process, the product in the form of fine powder was unloaded and sieved. A ternary compound material CoQ10/HPC/sucrose ester was obtained in a w/w ratio 1/0.5/1 with a 40% by weight CoQ10 titre.

Example 5: Composition of the Present Invention Obtained by Co-Grinding

Ternary Composition of CoQ10/HPC/Sucrose Ester 3/3/4.

For the preparation of the ternary composition of said example, 15 g of a mixture in w/w ratio 3/3/4 of CoQ10 (4.5 g, 30%) HPC (4.5 g, 30%) and sucrose ester (6 g, 40%), obtained for example using a rotating body mixer, were loaded into a jar of a planetary mill and subjected to mechano-chemical activation for 30 minutes at a speed of 200 rpm. At the end of the process, the product in the form of fine powder was unloaded and sieved. A ternary compound material CoQ10/HPC/sucrose ester was obtained in a w/w ratio 3/3/4 with a 30% by weight CoQ10 titre.

Example 6: Composition of the Present Invention Obtained by Spray Drying

Ternary Composition of CoQ10/HPC/Sucrose Ester 1/2/1.

HPC (15.0 g, 50%) was dispersed under stirring in 400 ml of ethanol to which sucrose ester (7.5 g, 25%) was added at room temperature. CoQ10 (7.5 g, 25%) was dissolved in 200 ml of methylene chloride and the solution added to the previous solution. The solution was spray-dried.

Example 7: Composition of the Present Invention Obtained by Spray Drying

Ternary Composition of CoQ10/HPC/Sucrose Ester 1/1/1.

HPC (10.0 g, 33.3%) was dispersed under stirring in 250 ml of ethanol to which sucrose ester (10.0 g, 33.3%) was added at room temperature. CoQ10 (10.0 g, 33.3%) was dissolved in 250 ml of methylene chloride and the solution added to the previous solution. The dispersion was spray-dried.

COMPARISON EXAMPLES

Examples A1-A4: State of the Art According to WO'028: Ternary Compositions of Q10/Maltodextrin/Sucrose Ester Obtained by Co-Grinding For the preparations of the ternary compositions of said comparison Examples A1-A4, 15 g of mixture of CoQ10/maltodextrin/sucrose ester in a ratio similar to those described in the Examples 1-4 respectively, were treated as in the corresponding Example 1, Example 2, Example 3, Example 4. For each comparative Example A1-A3 a CoQ10/maltodextrin/sucrose ester composite ternary material was obtained in a ratio and with a CoQ10 titre equal to those described in the Examples 1-3 (10, 25, 33.3%). Said materials are also described in WO'028 in the Examples 1, F1 and E1 respectively. It was not possible to recover a product with a title in CoQ10 equal to 40% (Example A4 in comparison with Example 4), since this was totally packed on the bottom of the jar.

Examples B2-B3: State of the Art According to WO'028: Ternary Compositions of Q10/HPMC/Sucrose Ester Obtained by Co-Grinding For the preparation of the ternary compositions of said Examples A1-A4, 15 g of mixture of CoQ10/maltodextrin/sucrose ester in a ratio similar to those described in the Examples 2 and 3 respectively, were treated as in the corresponding Example 2 and Example 3. For each comparative Examples B2-B3 a CoQ10/HPMC/sucrose ester composite ternary material was obtained in a ratio and with a titre in CoQ10 equal to those described in the Examples 1-3 (25, 33.3%). Said materials are also described in WO'028 in Examples D1 and C1 respectively.

Examples C1-C2: State of the Art According to WO'028: Ternary Compositions of Q10/Maltodextrin/Sucrose Ester Obtained by Spray-Drying The Examples 6 and 7 were replicated in the comparative Examples C1-C2 under the same conditions using maltodextrin instead of HPC. Said materials are also described in WO'028, in Examples F2 and E2 respectively.

Examples D1-D2: State of the Art According to WO'028: Ternary Compositions of Q10/HPMC/Sucrose Ester Obtained by Spray-Drying The Examples 6 and 7 were replicated in the comparative Examples D1-D2 under the same conditions using HPMC instead of HPC. Said materials are also described in WO'028, in the Examples D2 and C2 respectively.

Solubility Tests

The Applicant conducted tests to assess the solubility in water at 37° C. (physiological temperature) of the composition of the present invention, exemplified according to some Examples 1-5, and some comparison systems, such as Examples A1-A3 and B1-B3 and also on some simple physical mixtures of powders, both binary and ternary. The physical mixtures are obtained by weighing the components in the ratios indicated in the respective comparative examples and mixing them for 10 minutes in the shaker-rotary mixer.

For the analysis of the solubility, an excess of sample in powder is placed in water at 37° C., such as to have a bottom body.

After 1 hour with the analytical suitable method (for example spectrophotometry, UV, HPLC) the maximum amount of CoQ10 that passes into solution is measured. Table 1 below shows the results for Example 1, Example A1 and Example B1 (the abbreviation MDX stands for maltodextrin/s).

TABLE 1

| CoQ10 | Carrier | Solubility 1 hour (μg/ml) | | |
|---|---|---|---|---|
| | | Co-ground | Physical ternary mixtures | Binary Q10/carrier |
| Example 1 | HPC | 569 | 45 | 32 |
| Example A1 | MDX | 280 | 46 | 11 |
| Example B1 | HPMC | 130 | 43 | 56 |

From the above data, it is noted that the solubility of CoQ10 in the co-ground with HPC (Example 1) is more than double compared to that of the co-ground with MDX (Example A1) and more than 4 times the one with HPMC (Example B1).

This advantageous result is surprising and unexpected for many reasons, and briefly discussed here below:

1. HPC and HPMC are structurally similar and the simple binary physical mixtures with Q10 did not let to expect such an increase, on the contrary the solubility of the mixture with HPC was even lower than that with HPMC.

2. The physical ternary mixtures showed a slight increase compared to the binary with similar values, attributable to the emulsifying capacity of the sucrose ester. The absolute values were of an order of magnitude lower than the co-ground. The technical advantageous effect of the system Q10/HPC/sucrose ester was therefore not predictable on the basis of the sole emulsifying power obtained with sucrose ester.

3. The literature shows a better capacity of HPC compared to HPMC to sustain/extend drug delivery, so it was not predictable that it could increase the solubility. See for example in "Comparative Study of High Viscosity Grade of Hydroxypropyl Cellulose for Hydrophilic Matrix", Sustained Release Formulation Kenji Sugisawa, Satoru Abe, Shinichiro Tsue, Takeshi Shimotori, AAPS 2012, Annual Meeting Chicago: "HPC was found to sustain drug release more effectively than HPMC in the case of the equivalent viscosity" and also that "HPC was found to have equivalent control release performance to HPMC while its viscosity is much lower".

4. In WO'028 the authors speculated that "the best performance of the maltodextrin could be explained with a distribution of fine particulate components of maltodextrin, which is soluble in water and therefore, when it comes into contact with it, this helps the solubilization. Instead not only does the HPMC form gels, but, given the complete solubilization, when it is spray-dried, it englobes more intimately CoQ10 and releases it then more slowly, also due to the gelled layer."

The gelling capacity of HPC is not only comparable to that of HPMC, but, as discussed in paragraph 3 above, HPC is an excellent agent for the controlled release: so it was even less likely that the ternary system could be so soluble and so quickly. On this point, see also tests DRT (Dissolution Rate Test) further on.

5. Compared to WO'028 there is the significant technological advantage that you can get up to 40% Q10 percentages or higher, without incurring in the technological problems that you may encounter in WO'028 instead.

The unexpected and advantageous effect on the solubility is maintained at different ratios of Q10/HPC/sucrose esters, when compared with analogues of the state of the art. Significantly, this effect is maintained even if the ratio Q10/sucrose ester is different from 1/1, such as for Example 5. See the following Table 2.

TABLE 2

| CoQ10 | Solubility 1 hour (μg/ml) | Carrier | Physical ternary mixture | Binary Q10/carrier |
|---|---|---|---|---|
| Example 1 | 569 | HPC | 93 | 32 |
| Example 2 | 440 | HPC | | |
| Example 3 | 299 | HPC | | |
| Example 4 | 150 | HPC | | |
| Example 5 | 315 | HPC | | |
| Example A1 | 280 | MDX | 46 | 11 |
| Example A2 | 190 | MDX | | |
| Example A3 | 170 | MDX | | |
| Example B1 | 130 | HPMC | 43 | 56 |
| Example B2 | 130 | HPMC | | |
| Example B3 | 100 | HPMC | | |

Figure 1:
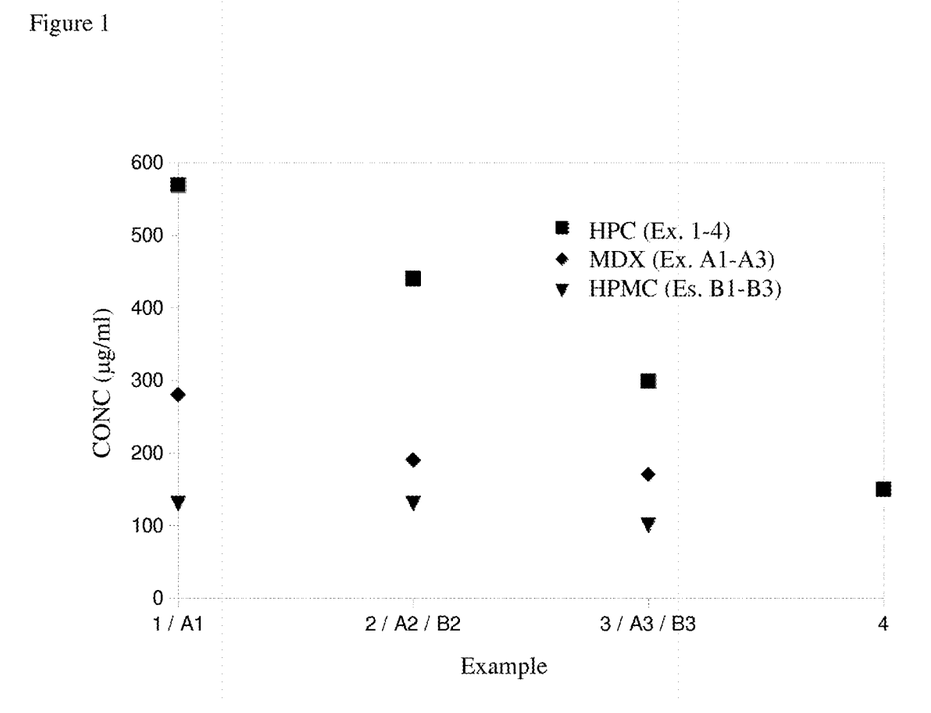
FIG. 1: it shows a comparison graph of the values shown in Table 2, i.e. the solubility values for Q10 after 1 hour (µg/ml) for the various compositions prepared according to the cited Examples. Each value refers to a composition prepared in a specific Example as reported on the X-axis and in the legend.

FIG. 1 shows a comparison graph of the values shown in Table 2. It can be seen that, with the increase in the percentage of the carrier, also the solubility increases. However, by increasing the percentage, the differential between solubility performances of the investigated carriers also increases. The Applicant, therefore, believes that there is a greater efficacy of the HPC/sucrose ester system combined with Q10 than the maltodextrin/sucrose ester system paired with Q10. The sensational difference between the HPC and HPMC also demonstrate how it was not possible to expect such a result given the structural similarity of the two materials.

Dissolution Rate Test (DRT)

The tests were carried out following the method described in WO'028, entirely incorporated herein by reference, weighing the powders, so as to always use 50 mg of CoQ10.

Figure 2:
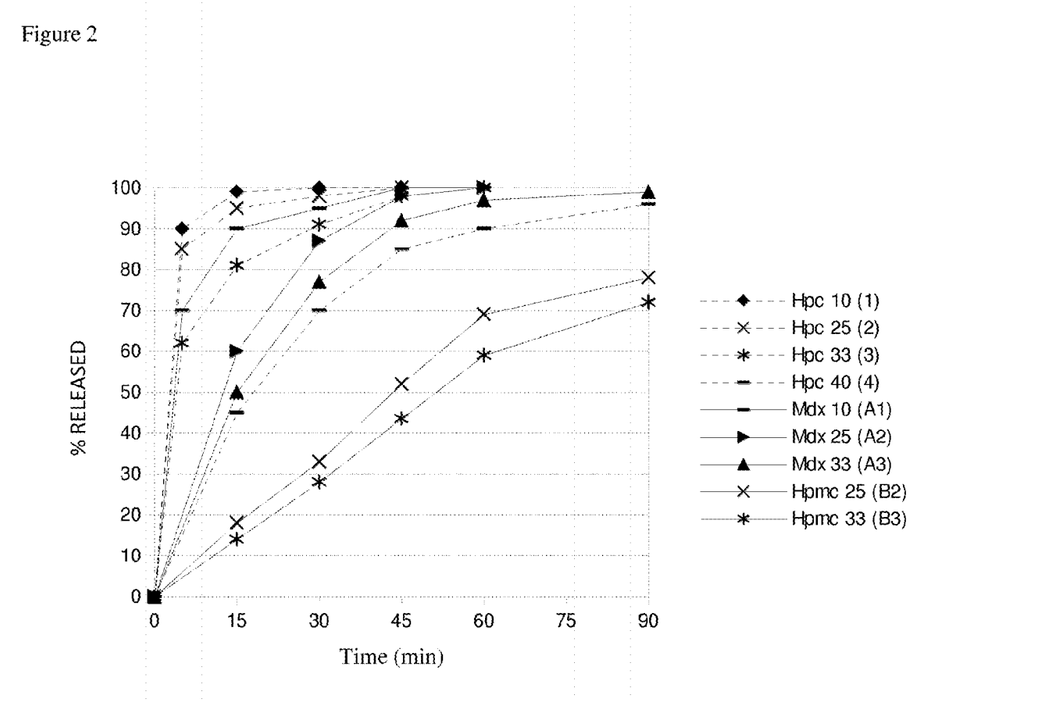

500 ml of pH 1.2 buffer were used added with 1% of Tween80 maintained at T=37° C. and under stirring at a speed of 50 rpm. Aliquots were taken at 15, 30, 60 and 120 minutes (for DRT of Example 1 aliquots were also taken at 5 minutes). Each aliquot was carried out by HPLC under the following conditions:

Detector: UV at 275 nm
Column: Zorbax Extend 300C18 or equivalent 4.6×150.5 μm
T column: 25° C.
Mobile phase: ethanol/methanol 20/80
Flow: 2.0 ml/min
RT: 8 min FIG. 2 shows the comparison graphs of DRT for co-ground: Examples 1-4 with HPC (dashed lines), Examples A1-A3, Examples B2-B3. In the legend in FIG. 2 the number after the acronym/name of the carrier indicates the % w/w CoQ10 and in brackets the example, to which the graph refers to.

From the graphs of FIG. 2 it appears that all co-ground with HPC (Examples 1-4) are faster than co-ground with MDX (Examples A1-A3).

The formulation with 25% w/w of HPC (Example 2) is even faster than the formulation with MDX and 10% w/w CoQ10 (Example A1).

The formulation with 33% w/w of HPC (Example 3) is comparable to the formulation with MDX and 25% w/w CoQ10 (Example A2).

The formulation with 40% w/w of HPC (Example 4) is comparable to the formulation with MDX and 33% w/w CoQ10 (Example A3).

The formulation with MDX and 40% w/w CoQ10 cannot be obtained.

Moreover, it is confirmed that the formulations with HPMC give lower performances, as already described in WO'028.

Figure 3:
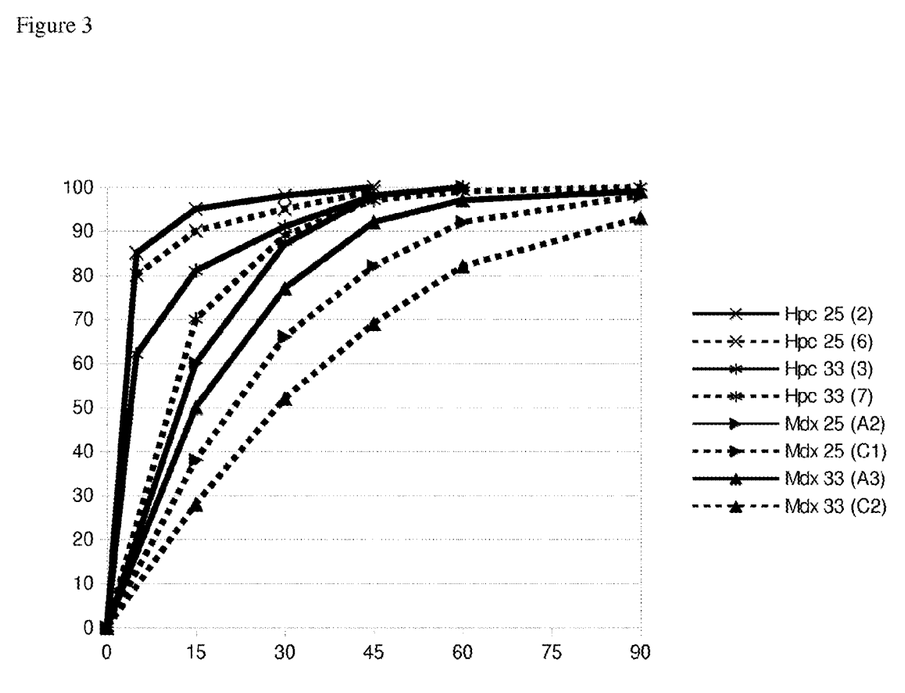

FIG. 3 shows the comparison graphs of DRT between co-ground and spry-dried (HPC-MDX): Examples 2, 3, 6, 7 with HPC, Examples A2-A3 and Examples C1-C2 with MDX. In FIG. 3, the solid lines identify the graphs of the co-ground formulations, while the dotted lines identify the graphs of the spray-dried formulations. Also in the legend in FIG. 3 the number after the acronym/name of the carrier indicates the w/w % CoQ10 and the one between brackets the example to which the graph refers to.

From the values shown in the graphs of FIG. 3 it shows that the formulations obtained by spray-drying have always lower performances than the corresponding co-ground formulations, as also described in WO'028. However, surprisingly, it is noticed that the spray-dried formulations with HPC have improved properties compared to co-ground formulations with MDX. See for example the spray-dried formulation with HPC and 25% w/w CoQ10 (Example C1), which is faster than the co-ground formulation with HPC and 25% w/w CoQ10 (Example A2).

Figure 4:
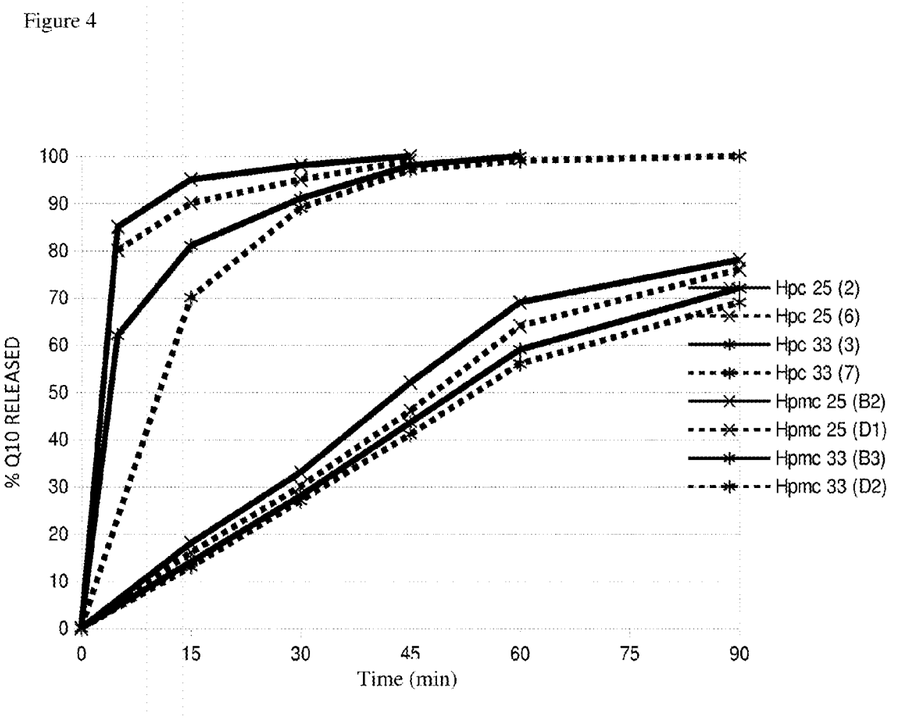

FIG. 4 shows the comparison graphs of DRT between co-ground and spry-dried (HPC-HPMC): Examples 2, 3, 6, 7 with HPC, Examples B2-B3 and Examples D1-D2 with HPMC. In FIG. 4, the solid lines identify the graphs of the co-ground formulations, while the dotted lines identify the graphs of the spray-dried formulations. Also in the legend in FIG. 4 the number after the acronym/name of the carrier indicates the w/w % CoQ10 and the one between brackets the example to which the graph refers to. Also these comparison data confirm what has already been discussed. Moreover, it is confirmed what has already been said. Furthermore, although in WO'028 it is claimed that " . . . the compositions with HPMC fail to release 100% of CoQ10 within the 120 minutes of the test, probably because the HPMC tends to gel", the data presented here demonstrate that HPC, despite what has already been discussed with regard the thickening/gelling capacity, instead releases 100% of CoQ10.

It is clear that to the CoQ10 based composition described so far, modifications and/or additions of parts can be made, without by this departing from the scope of the present invention as defined by the claims.

It is also clear that, although the present invention has been described with reference to some specific examples, a person skilled in the art will surely be able to implement many other equivalent forms of CoQ10 based compositions, having the characteristics expressed in the claims and therefore all encompassed in the field of protection defined by them.

Although the above description relates to embodiments of the invention, other and further embodiments can be envisaged without thereby departing from the main scope of protection, and its scope of protection is defined by the claims that follow.

The invention claimed is:

1. A formulation comprising a ternary composition, consisting of CoQ10, one or more hydroxypropylcellulose (HPC) based amphiphilic carriers and one or more adjuvants selected from the group consisting of sucrose esters, the ternary composition being formed by dry co-grinding of the CoQ10, the one or more hydroxypropylcellulose (HPC) based amphiphilic carriers and the one or more adjuvants selected from the group consisting of sucrose esters.

2. The formulation of claim 1, wherein the weight ratio of CoQ10 to the sucrose ester in the ternary composition is from 0.5:1 to 6:1.

3. The formulation of claim 1, wherein the amount of CoQ10 in the ternary composition is between 10% and 60% by weight.

4. The formulation of claim 1, wherein the amount of the one or more HPC based amphiphilic carriers in the ternary composition is between 10% and 80% by weight.

5. The formulation of claim 1, wherein the amount of the one or more adjuvants selected from the group consisting of sucrose esters in the ternary composition is between 10% and 40% by weight, and wherein the sucrose ester is selected from the group consisting of sucrose monopalmitate, sucrose monostearate, sucrose dipalmitate, sucrose distearate, and mixtures thereof.

6. The formulation of claim 1, wherein the one or more adjuvants selected from the group consisting of sucrose esters in the ternary composition has an HLB value between 14 and 16.

7. The formulation of claim 1, wherein the formulation is selected from the group consisting of: creams, ointments, gels, pastes, water-based creams, emulsions, serums, face powders, sprays, suppositories, ovules, transdermal patches, toothpastes, periodontal gels and mouthwashes.

8. The formulation of claim 1, wherein the formulation further comprises one or more of the following substances:
a) vitamin A, B1, vitamin B2, vitamin B3, vitamin B5, vitamin B6, vitamin B12, vitamin C, vitamin D, vitamin E, and vitamin H, b) magnesium potassium, zinc, selenium, calcium, fluorine, phosphorus, iron, and iodine, c) lactoferrin, berberine, berberine hydrochloride, silymarin, monacolin, folic acid, astaxanthin, policosanol(s), sinesetin, essential omega-3 fatty acids, EPA, DHA, omega-6 fatty acids, resveratrol, L-carnitine, acetyl L-carnitine, propionyl L-carnitine, acetyl L-carnitine taurinate, L-carnitine tartrate, creatine, carnosine, L-aspartic acid, L-asparagine, Monascus purpureus, diosmin, hesperidin, troxerutin, glutamine, phosphoserine, Gingko *biloba* and caffeine.

9. The formulation of claim 8, wherein the formulation is selected from the group consisting of: creams, ointments, gels, pastes, water-based creams, emulsions, serums, face powders, sprays, suppositories, ovules, transdermal patches, toothpastes, periodontal gels and mouthwashes.

10. The formulation of claim 1, wherein the weight ratio of the CoQ10 to the sucrose ester in the ternary composition is from 0.5:1 to 5:1.

11. The formulation of claim 1, wherein the weight ratio of the CoQ10 to the sucrose ester in the ternary composition is from 0.5:1 to 4:1.

12. The formulation of claim 1, wherein the weight ratio of the CoQ10 to the sucrose ester in the ternary composition is from 0.5:1 to 3:1.

13. The formulation of claim 1, wherein the CoQ10 is present in an amount of between 10% and 55% by weight in the ternary composition.

14. The formulation of claim 1, wherein the CoQ10 is present in an amount of between 25% and 50% by weight in the ternary composition.

15. The formulation of claim 1, wherein the CoQ10 is present in an amount of between 30% and 40% by weight in the ternary composition.

16. The formulation of claim 1, wherein the one or more HPC based amphiphilic carriers is present in the ternary composition in an amount of between 20% and 70% by weight.

17. The formulation of claim 1, wherein the one or more HPC based amphiphilic carriers is present in the ternary composition in an amount of between 30% and 60% by weight.

18. The formulation of claim 1 wherein the one or more HPC based amphiphilic carriers is present in the ternary composition in an amount of between 40% and 50% by weight.

19. The formulation of claim 1, wherein the sucrose ester is present in the ternary composition in an amount of between 20% and 30% by weight.

20. The formulation of claim 1, in a form suitable for oral administration.

21. The formulation of claim 8, in a form suitable for oral administration.

22. The formulation of claim 1, wherein the formulation consists of the ternary composition and packaging material.

23. A method comprising administering the formulation of claim 1 to a subject with a cardiovascular disease or condition, wherein the cardiovascular disease or condition is selected from the group consisting of:
- post-AMI (acute myocardial infarction) and post-PTCA (percutaneous transluminal coronary angioplasty) or coronary post-surgery in the prevention of reperfusion damages and in the myocardial oxygenation;
- congestive heart failure (CHF) for the improvement of inotropism and the ventricular ejection fraction (VEF);
- chronic dyslipidaemia in subjects undergoing treatment with statins; or cardiotoxicity from chemotherapeutical and/or radio therapeutic agent;
- post-surgery asthenia in patient at high cardiovascular risk (CV), in elderly patient and in oncological patient;
- asthenia in cardiac, neurological and/or orthopaedic patient undergoing functional rehabilitation; and
- chronic asthenia from cardio circulatory and muscular deficit in elderly subjects.

* * * * *